(12) United States Patent
Siegert (10) Patent No.: US 11,691,901 B2
(45) Date of Patent: Jul. 4, 2023

(54) BIOELECTROCHEMICAL METHOD AND APPARATUS FOR ENERGY RECLAMATION FROM NITROGEN COMPOUNDS

(71) Applicant: HEXEM SA, Port-Valais (CH)

(72) Inventor: Michael Siegert, Lausanne (CH)

(73) Assignee: HEXEM SA

( * ) Notice: Subject to any disclaimer, the term of this patent is extended or adjusted under 35 U.S.C. 154(b) by 134 days.

(21) Appl. No.: 16/760,424

(22) PCT Filed: Oct. 29, 2018

(86) PCT No.: PCT/CA2018/051366
§ 371 (c)(1),
(2) Date: Apr. 29, 2020

(87) PCT Pub. No.: WO2019/079908
PCT Pub. Date: May 2, 2019

(65) Prior Publication Data
US 2020/0339453 A1    Oct. 29, 2020

Related U.S. Application Data

(60) Provisional application No. 62/578,456, filed on Oct. 29, 2017.

(51) Int. Cl.
*C02F 3/00* (2023.01)
*C02F 1/46* (2023.01)
(Continued)

(52) U.S. Cl.
CPC .............. *C02F 3/005* (2013.01); *C02F 1/461* (2013.01); *C02F 3/006* (2013.01); *C02F 3/341* (2013.01);
(Continued)

(58) Field of Classification Search
CPC .......... C02F 3/005; C02F 3/006; C02F 3/341; C02F 2101/16; C02F 2101/38;
(Continued)

(56) References Cited

U.S. PATENT DOCUMENTS 5,360,522 A    11/1994   Kuroda et al.
6,485,646 B1   11/2002   Dijkman et al.
(Continued)

FOREIGN PATENT DOCUMENTS

CN    104743663 A    7/2015
EP    0573226 A1    12/1993
(Continued)

OTHER PUBLICATIONS

English translation of Konami et al Patent Publication JP2005296905A, published Oct. 2005 (Year: 2005).*
(Continued)

*Primary Examiner* — Joseph W Drodge
(74) *Attorney, Agent, or Firm* — Marshall, Gerstein & Borun LLP (57) ABSTRACT

Methods are described for treating aqueous solutions, including wastewater, to remove nitrogen-containing compounds using electrochemical processes. The method may be conducted electrolytically under an applied voltage or using endogenous current in a fuel cell arrangement. In some embodiments, energy is reclaimed in the form of hydrogen, methane, and other hydrocarbons or organic molecules. Microorganisms may be used as the catalyst for oxidation of the nitrogen-containing compound and/or reduction of hydrogen ions, carbon dioxide, or bicarbonate. Anaerobic or low-oxygen conditions may be used in the zone.

4 Claims, 7 Drawing Sheets

(51) Int. Cl.
| | |
|---|---|
| *H01M 8/16* | (2006.01) |
| *H01M 8/22* | (2006.01) |
| *C02F 3/34* | (2023.01) |
| *C02F 1/461* | (2023.01) |
| *C02F 101/16* | (2006.01) |
| *C02F 101/38* | (2006.01) |

(52) U.S. Cl.
 CPC ............ *H01M 8/16* (2013.01); *H01M 8/222* (2013.01); *C02F 2101/16* (2013.01); *C02F 2101/38* (2013.01); *C02F 2303/10* (2013.01); *C02F 2305/06* (2013.01)

(58) Field of Classification Search
 CPC .... C02F 2303/10; C02F 2305/06; C02F 1/46; C02F 1/46109; C02F 1/586; C02F 1/72; C02F 2001/46133; C02F 1/461; C02F 1/70; H01M 8/16; H01M 8/222; Y02E 50/30; Y02E 60/50; Y02W 10/30; Y02W 10/37; G01N 2333/906; G01N 33/5438; C12Q 1/02
 See application file for complete search history.

(56) References Cited

U.S. PATENT DOCUMENTS

| | | | |
|---|---|---|---|
| 8,440,438 B2 | 5/2013 | Cheng et al. | |
| 8,524,402 B2 | 9/2013 | He et al. | |
| 9,428,745 B2 | 8/2016 | Mets | |
| 9,725,812 B2 | 8/2017 | Kuntke et al. | |
| 2011/0024361 A1* | 2/2011 | Schwartzel | C02F 1/467 204/290.01 |
| 2013/0256149 A1* | 10/2013 | Popat | C25B 1/04 204/260 |
| 2014/0054209 A1* | 2/2014 | Adams | C02F 3/005 210/150 |
| 2014/0353170 A1 | 12/2014 | Huang et al. | |
| 2015/0017089 A1 | 1/2015 | Kuntke et al. | |
| 2015/0266753 A1* | 9/2015 | Fraim | C02F 1/467 204/290.01 |
| 2018/0230033 A1* | 8/2018 | Cumbie | C02F 3/2866 |

FOREIGN PATENT DOCUMENTS

| | | | | |
|---|---|---|---|---|
| JP | 2005296905 A | * | 10/2005 | ............... B09B 3/00 |
| WO | WO2005058761 A1 | * | 6/2005 | ............... C02F 1/461 |
| WO | WO-2013105854 A1 | | 7/2013 | |
| WO | WO-2014172791 A1 | | 10/2014 | |

OTHER PUBLICATIONS

International Search Report and Written Opinion for PCT/CA2018/051366, dated Nov. 28, 2018.

Xinxin Ju et al; "Intensified nitrogen and phosphorus removal in a novel electrolysis-integrated tidal flow constructed wetland system" Water Research 59, 2014, pp. 37-45.

Xinxin Ju et al; "How the novel integration of electrolysis in tidal flow constructed wetlands intensifies nutrients removal and odor control" Bioresource Technology 169, pp. 605-613, 2014.

Van Lier et al; "Development of Anaerobic High-rate Reactors, Focusing on Sludge Bed Technology" Adv. Biochem. Eng. Biotchnol., 2016.

Virdis et al; "Microbial fuel cells for simultaneous carbon and nitrogen removal" Water Research, vol. 42, Issue 12, 2008, pp. 3013-3024.

Strous; "The anammox case—A new experimental manifesto for microbiological eco-physiology" Antoine van Leeuwenhoek, vol. 81, 2002, pp. 693-702.

Vilajeliu-pons et al; "Microbial electricity driven anoxic ammonium removal" Water Research 130, 2018, pp. 168-175.

Zhan, G et al. "Anodic ammonium oxidation to nitrogen gas catalyzed by mixed biofilms in bioelectrochemical systems" Electrochimica Acta, vol. 135, 2014, pp. 345-350.

Zhan; "Autotrophic nitrogen removal from ammonium at low applied voltage in a single-compartment microbial electrolysis cell" Bioresource Technology 116, 2012, pp. 271-277.

Virdis et al; "Biofilm stratification during simultaneous nitrification and denitrification (SND) at a biocathode" Bioresource Technology, vol. 102, Issue 1, 2011, pp. 334-341.

Virdis et al.; "Simultaneous nitrification, denitrification and carbon removal in microbial fuel cells" Water Research, vol. 4, Issue 9, 2010, pp. 2970-2980.

Rosenwinkle et al; "Deammonification in the Moving-Bed Process for the Treatment of Wastewater with High Ammonia Content", Chemical Engineering & Technology, vol. 28, Issue 1, 2005.

Villano, M et al. "Bioelectrochemical reduction of CO2 to CH4 via direct and indirect extracellular electron transfer by hydrogenophilic methanogenic culture." Bioresource Technology, vol. 101, Issue 9, 2010, pp. 3085-3090.

Clauwaert et al., "Methanogenesis in membraneless microbial electrolysis cells," Applied Microbiology and Biotechnology, vol. 82, No. 5, pp. 829-836, 2009.

Extended European Search Report for EP 18870505.7, dated Jul. 12, 2021.

* cited by examiner

BIOELECTROCHEMICAL METHOD AND APPARATUS FOR ENERGY RECLAMATION FROM NITROGEN COMPOUNDS

This application claims priority based on U.S. Application No. 62/578,456 entitled "Processes for Energy Reclamation from Nitrogen Removal From Liquids and for Electrical Current Production" filed on Oct. 29, 2017, which is herein incorporated by reference in its entirety.

TECHNICAL FIELD

The present disclosure relates to the field of nitrogen removal from solutions. More specifically, the present disclosure relates to the removal of ammonium or amines of wastewater.

BACKGROUND

Wastewater and other solutions often contain nitrogen-containing compounds that must be disposed of. For wastewater, ammonium removal is important for proper discharge in order to minimize environmental damage. Other disposal needs also arise in situations where nitrogen-containing compounds are dissolved in solution, but no longer wanted.

Conventional approaches for removing nitrogen from aqueous solutions rely on oxygen saturation in order to convert nitrogen-containing compounds, such as ammonium and amines, into nitrate (nitrification) which subsequently converted into gaseous nitrogen ($N_2$, denitrification). However, oxygen does not dissolve well in solution, making nitrogen removal an energy intensive process. Moreover, oxygen is a strong oxidant, which consumes much of the available chemical energy as heat, resulting in a process that is energy inefficient.

A particular challenge of oxidizing nitrogen-containing compounds is the strong bond energy that all nitrogen atoms have. In biological systems, this is overcome by using strong oxidants such as $O_2$, $NO_3^-$, $NO_2^-$. Alternative approaches for nitrogen removal of aqueous solutions still require the presence of oxygen, either directly or indirectly.

For example, in the "annamox" process, a portion of the ammonium ions are first oxidized to nitrite using molecular oxygen. Microorganisms then react the nitrite ions with the balance of the ammonium ions in solution, to produce nitrogen gas ($N_2$). However, this process is slow, requires high solution volumes, operates under a narrow range of temperature and pH, requires excess nitrate or nitrite that must still be disposed of, and does not recapture energy from ammonium.

Another approach for nitrogen removal is microbial electrolysis, in which one or more electrodes are covered in a biofilm or are placed in a suspension of microorganisms. Examples of this approach are described by Kuntke et al. in U.S. Pat. No. 9,725,812 and Kuroda et al. in European Patent No. 0573226. In such approaches, the microorganisms that remove contaminants from the water are offered a small energetic incentive in the form of an electrochemical potential, which they can use for their metabolism. In exchange, the microorganisms catalyse the oxidation of ammonium, nitrate, or nitrite into $N_2$. Nevertheless, such approaches also rely on aerated conditions in order to achieve complete nitrogen removal, which substantially reduces the energy available for recapture of useful compounds from the treated solution, such as hydrogen gas, at the cathode. Moreover, the complexity of such systems, which typically require three or more electrochemically active electrodes, makes them expensive to manufacture and operate. Finally, such systems have not been successful in removing nitrogen at lower concentrations, such as ammonium concentrations below 0.5 g/L.

Various compounds of interest may also be recovered from aqueous solutions during electrolysis. For example, hydrogen gas can be produced at the cathode by reducing $H^+$ ions in water, whereas methane can be produced at the cathode by reducing bicarbonate ions. Considering that a well developed infrastructure exists for methane transport and storage, as opposed to hydrogen gas, methane is preferred as an energy storage medium.

This background information is provided for the purpose of making known information believed by the applicant to be of possible relevance to the present disclosure. No admission is necessarily intended, nor should be construed, that any of the preceding information constitutes prior art against the present disclosure.

SUMMARY

The present disclosure provides an electrochemical process for removal of nitrogen-containing compounds from solutions, such as wastewater. Fuel cells are also discussed, in which some or all of the voltage is provided by electrogenic microorganisms.

Oxygen is not directly involved in the removal of the nitrogen-containing compound, which allows for the extraction of a portion of the energy contained in said nitrogen-containing compounds.

Microorganisms living in wastewater, or supplied using an external microbial suspension capable of such a process, use the nitrogen-containing compounds to produce electrical current. This process may be assisted by a power source (electrolysis cell) or a chemical electron acceptor across an electrical circuit (fuel cell).

Various nitrogen-containing compounds are contemplated within the scope of the present disclosure, and are defined further below. Such compounds may be oxidized completely to nitrogen gas, or incompletely to other oxidized nitrogen compounds such as $N_4O$, $N_2O$, NO, $N_2O_3$, $NO_2$, $N_2O_4$, $N_2O_5$, $NO_3$, $NO_2^-$, $NO_3^-$, cyanides such as HCN, or various organic nitrogen oxides. In embodiments where nitrogen-containing compounds are fully oxidized, the production of toxic intermediates is reduced.

The disclosed methods produce either useful chemicals when operated in electrolysis mode or electrical power when operated in fuel cell mode. In either case, the energy efficiency of the process may be significantly increased.

In embodiments where methane is produced, the energy recaptured from the solution being treated can be stored using existing energy infrastructure to produce liquid fuels. Liquid fuels or their precursors may also be produced from the generated methane. Brittling of metals is also decreased. Aside from its energy uses, methane can also be used as a carbon feedstock for the chemical industry, or as an alternative source of hydrogen. The resulting biogas may also be of higher quality due to the absence of $CO_2$ production in the cathodic reaction. Recycling of $CO_2$ production into methane may also reduce greenhouse gases during the treatment process.

In one broad aspect, there is provided a method for treating an aqueous solution using an electrolytic cell having a first electrode in electrical communication with a second electrode. The method includes the steps of: disposing the aqueous solution within a reaction zone in the electrolytic cell, with effect that the aqueous solution is in electrical communication with the first electrode; and applying a voltage across the first and second electrodes, with effect that at least one nitrogen-containing compound, of the aqueous solution, is oxidized. The reaction zone less than 100 µmol L-1 of free oxygen.

In another broad aspect, there is provided a method for treating an aqueous solution using an electrolytic cell having a first electrode in electrical communication with a second electrode. The method includes the steps of: disposing the aqueous solution within a reaction zone in the electrolytic cell, with effect that the aqueous solution is in electrical communication with the first electrode; and applying a voltage across the first and second electrodes, with effect that at least one nitrogen-containing compound, of the aqueous solution, is oxidized. The reaction zone is an anaerobic environment.

In another broad aspect, there is provided a method of treating wastewater. The method includes a reactive process, including within a reaction zone, disposing an operative mixture, including operative wastewater, in communication with an oxidant, with effect that at least one nitrogen-containing compound, within the operative wastewater, become oxidized. The oxidant includes carbon dioxide.

In another broad aspect, there is provided a method of treating wastewater. The method includes supplying wastewater to a reaction zone such that wastewater becomes disposed in communication with operative microorganisms within the reaction zone, with effect that: (i) produced $CO_2$, is obtained, and (ii) one or more nitrogen-containing compounds, within the wastewater, interact with operative $CO_2$, including the produced $CO_2$ and any $CO_2$ within the supplied wastewater, with effect that the one or more nitrogen-containing compounds are oxidized.

In another broad aspect, there is provided a method of generating electric current within an external circuit of a fuel cell having a first electrode and a second electrode, the first electrode being coupled to the second electrode via the external circuit. The method includes: disposing operative wastewater in electrical communication with the first electrode within a first space of the fuel cell, and disposing an oxidant in electrical communication with the second electrode within a second space of the fuel cell.

In an embodiment, the reaction zone contains less than 100 µmol $L^{-1}$ of free oxygen, less than 80 µmol $L^{-1}$ of free oxygen, less than 50 µmol $L^{-1}$ of free oxygen, or less than 30 µmol $L^{-1}$ of free oxygen. There may also be an absence, or substantial absence, of free oxygen within the reaction zone. The oxygen conditions in the reaction zone may also apply to the electrolytic cell as a whole.

In an embodiment, the first electrode is an anode and the second electrode is a cathode, which are in electrical communication with one another. A voltage may be applied between the anode and the cathode that is between 10 mV and 2500 mV. The anode potential may be at least +400 mV, +400 mV, between +400 mV and +550 mV, at least +500 mV, +500 mV, +550 mV, or other suitable voltages.

In an embodiment, the solution containing the at least one nitrogen-containing compound is wastewater, such as municipal wastewater. The at least one nitrogen-containing compound may be oxidized with effect that gaseous nitrogen is produced.

In an embodiment, a plurality of microorganisms are disposed within the reaction zone, which may be in suspension or located on the first electrode. Such microorganisms may be derived from ocean sediment, anaerobic digester sludge, or other sources.

In an embodiment, the cell comprises a first portion and a second portion, wherein the first electrode is disposed within the first portion and the second electrode is disposed within the second portion. An ion-exchange membrane may separate the first and second portions.

In an embodiment, the cell includes an oxidant at the second electrode, which may be disposed in a second reaction zone. The oxidant may include hydrogen ions that are reduced to hydrogen gas. Alternatively, or in addition, carbon dioxide or bicarbonate may be reduced to an organic compound, such as a hydrocarbon, including methane gas. The resulting hydrogen and/or methane gas may be collected and stored.

In another broad aspect, there is provided a method of detecting a target material within wastewater. The method includes disposing operative wastewater, including the target material, in electrical communication with a first electrode within a first space of a galvanic cell. An oxidant is disposed in electrical communication with a second electrode within a second space of the galvanic cell. The wastewater, the oxidant, the first electrode, and the second electrode co-operate to generate an electrical current within an external circuit of the galvanic cell. The generated current is sensed and in response to the sensing, a signal is transmitted, representative of the detection of the target material. In an embodiment, a method of treating the wastewater is initiated in response to the signal.

In another broad aspect, there is provided a method of treating wastewater. The method includes: disposing operative wastewater, including the target material, in electrical communication with a first electrode within a first space of a galvanic cell; and disposing an oxidant in electrical communication with a second electrode within a second space of the galvanic cell; wherein the wastewater, the oxidant, the first electrode, and the second electrode co-operate to generate an electrical current within an external circuit of the galvanic cell; sensing the generated current; and in response to the sensing, modulating a treatment of the wastewater.

In an embodiment, the modulating includes initiating the treatment of the wastewater, suspending the treatment of the wastewater, increasing a stimulus applied to the wastewater for the treatment of wastewater, or decreasing a stimulus applied to the wastewater for the treatment of wastewater.

DETAILED DESCRIPTION

To gain a better understanding, the following illustrative embodiments are set forth. It will be understood that these embodiments are intended to describe examples only and are not intended to limit the scope of the present disclosure in any way.

Definitions

"microorganisms" includes bacteria archaea, and eukarya of the genera: *Acidobacterium, Geothrix, Holophaga, Mycobacterium, Microbacterium, Marinobacter, Paludibacter, Petrimonas, Proteiniphilum, Sediminibacterium, Anaerolinea, Leptolinea, Caldilinea, Deinococcus, Thermus, Clostridium, Bacillus, Butyribacterium, Sporomusa, Acetobacterium, Acetogenium, Thermoanaerobacter, Anaerovorax, Desulfosporosinus, Proteiniborus, Faecalibacterium, Fastidiosipila, Hydrogenoanaerobacterium, Oscillibacter, Phascolarctobacterium, Turicibacter, Nitrospira, Nitrososphaera, Nitrosopumilus, Nitrobacter, Kuenenia, Brocardia, Nitrosomonas, Nitrosopumilus, Nitrosococcus, Nitrospina, Pirellula, Brevundimonas, Bradyrhizobium, Hyphomicrobium, Pedomicrobium, Xanthobacter, Methylosinus, Nordella, Rhodobium, Amaricoccus, Rhodobacter, Roseomonas, Botryococcus, Synechococcus, Synechocystis, Chloroflexus, Chlorobium, Sphingobium, Sphingomonas, Sphingopyxis, Chitinimonas, Ralstonia, Comamonas, Methylibium, Ottowia, Pelomonas, Herbaspirillum, Thiobacillus, Methylobacillus, Neisseria, Gallionella, Nitrosomonas, Azovibrio, Dechloromonas, Methyloversatilis, Propionivibrio, Kuenania, Thauera, Bdellovibrio, Desulfobacterium, Desulfobulbus, Desulfovibrio, Desulfuromonas, Geobacter, Anaeromyxobacter, Haliangium, Desulfobacca, Smithella, Syntrophus, Syntrophobacter, Syntrophorhabdus, Sulfurospirillum, Sulfuricurvum, Wolinella, Aeromonas, Haliea, Citrobacter, Methylobacter, Methylocaldum, Methylomonas, Methylosinus, Acinetobacter, Pseudomonas, Dokdonella, Thermomonas, Exilispira, Aminiphilus, Kosmotoga, Verrucomicrobia, Opitutus, Puniceicoccus, Tissierella, Sphingopyxis, Pseudoxanthomonas, Sterolibacterium, Brucella, Bosea, Brevundimonas, Singulisphaera, Azospira, Gemmatimonas, Sphingobacterium, Azonexus, Aquamicrobium, Petrimonas, Fontibacter, Arcobacter, Chryseobacterium, Megasphera, Truepera, Hydrogenophaga, Paracoccus, Stenotrophomonas, Methanobacterium, Methanobrevibacter, Methanothermobacter, Methanothermus, Methanomicrobium, Methanogenium, Methanoplanus, Methanoplanus, Methanolacinia, Methanocorpusculum, Methanofollis Methanolinea, Methanoculleus, Methanosphaerula, Methanolinea, Methanospirillum, Methanoregula, Methanofollis, Methanocalculus, Methanothrix, Methanosarcina, Methanosaeta, Methanosphaera, Halomethanococcus, Methanohalobium, Methanosalsum, Methanomethylovorans, Methanimicrococcus, Methanohalophilus, Methanolobus, Methanococcoides, Methanococcus, Methanoflorens, Methanohalophilus, Methanopyrus, Halobacterium, Thermococcus, Pyrococcus, Thermoproteus,* and *Saccharomyces*.

"nitrogen-containing compound" includes various organic and inorganic molecules containing nitrogen groups, such as amines, including without limitation ammonium, ammonium hydroxide, ethyl amine, hydroxyl amine, benzyl amine, and various organic nitrogen compounds including urea, trimethyl amine, ethyl amine, ethanolamine, or natural and artificial amino acids such as alanine, glutamine, arginine, cysteine, and serine. In some embodiments, the nitrogen-containing compound may also be drugs such as paracetamol, oxetacaine, chlorphenamine, chlorpromazine, amphetamine, clomipramine, or nortriptyline. Other nitrogen-containing compounds may be amides and alkylated amides such as acetamide, formamide, sulfonamide, phosphoramide, N-methylacetamide, or acrylamide. Additional nitrogen-containing compounds include glucosamines, for example glucosamine or N-acetylglucosamine or polymers of N-acetylglucosamine, such as chitin and peptidoglycan. Further nitrogen-containing compounds include nucleotides, deoxynucleotides, and purines or pyrimidines such as adenine, uridine, guanine, cytosine, and thymine. The nitrogen-containing compound may also be a polymer of the foregoing, such as polyamines, polyamides, or polynucleotides (e.g. RNA or DNA).

Example 1

Electrolytic Nitrogen Removal Coupled to Hydrogen Gas Production

Figure 1:
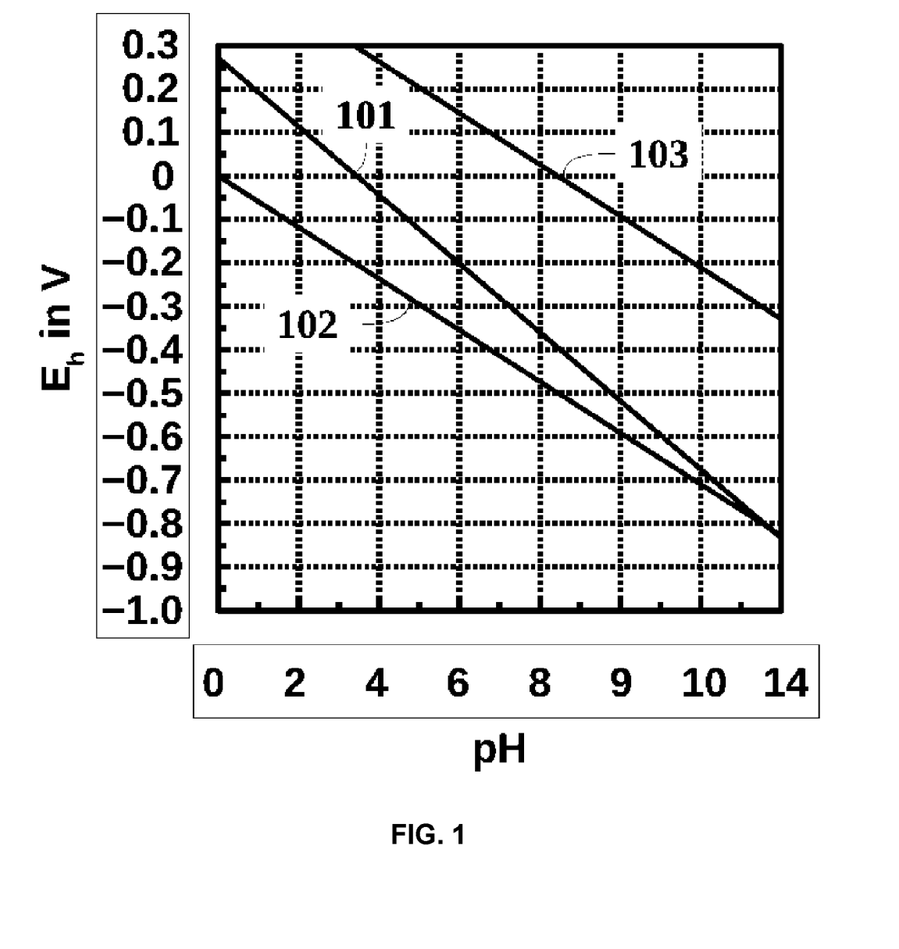
FIG. 1 is a Pourbaix diagram showing the relationship between pH and the redox potentials $E_h$ of ammonium oxidation (102), proton reduction (101), and proton reduction at +0.5 volts (103) versus a standard hydrogen electrode.

FIG. 1 is a Pourbaix diagram showing the relationship between pH on the X-axis and the redox potentials $E_h$ on the Y-axis of ammonium oxidation (101) and proton reduction (102). Also shown is the hypothetical offset potential (103) of proton reduction at +0.5 Volts versus a standard hydrogen electrode.

Under the standard conditions (all concentrations, except protons, 1 M, gases 1 bar, temperature 25° C.) shown in FIG. 1, the oxidation of dissolved ammonium 101 ($N_2/NH_4^+$) with protons 102 ($H^+/H_2$) as electron acceptor is not spontaneous. This is true for pH values (X-axis) between 0 and 14.

TABLE 1

Gibbs Free Energy of the complete reactions for oxidation of various nitrogen-containing compounds using protons as the oxidant:

| Net reaction | | | $\Delta G^{o\prime}$ kJ mol$^{-1}$ |
|---|---|---|---|
| Ammonium | | | |
| $2\ NH_4^+$ | $\rightarrow$ | $N_2 + 2\ H^+ + 3\ H_2$ | +40 |
| $3\ NH_4^+$ | $\rightarrow$ | $N_3^- + 4\ H^+ + 4\ H_2$ | +407 |

TABLE 1-continued

Gibbs Free Energy of the complete reactions for oxidation of various nitrogen-containing compounds using protons as the oxidant:

| Net reaction | | | $\Delta G^{\circ\prime}$ kJ mol$^{-1}$ |
|---|---|---|---|
| $2\ NH_4^+ + H_2O$ | $\rightarrow$ | $N_2O + 2\ H^+ + 4\ H_2$ | +420 |
| $2\ NH_4^+ + 2\ H_2O$ | $\rightarrow$ | $2\ NO + 2\ H^+ + 5\ H_2$ | +729 |
| $NH_4^+ + 2\ H_2O$ | $\rightarrow$ | $NO_2^- + 2\ H^+ + 3\ H_2$ | +437 |
| $2\ NH_4^+ + 3\ H_2O$ | $\rightarrow$ | $N_2O_3 + 2\ H^+ + 6\ H_2$ | +933 |
| $2\ NH_4^+ + 4\ H_2O$ | $\rightarrow$ | $N_2O_4 + 2\ H^+ + 7\ H_2$ | +1,128 |
| $2\ NH_4^+ + 4\ H_2O$ | $\rightarrow$ | $2\ NO_2 + 2\ H^+ + 7\ H_2$ | +1,130 |
| $NH_4^+ + 3\ H_2O$ | $\rightarrow$ | $NO_3^- + 2\ H^+ + 4\ H_2$ | +600 |
| $2\ NH_4^+ + 5\ H_2O$ | $\rightarrow$ | $N_2O_5 + 2\ H^+ + 8\ H_2$ | +1,382 |
| Ethyl Amine | | | |
| $2\ H_3C-CH_2NH_3^+ +$ $12\ H_2O$ | $\rightarrow$ | $N_2 + 4\ HCO_3^- +$ $6\ H^+ + 15\ H_2$ | +187 |
| $2\ H_3C-CH_2NH_3^+ +$ $6\ H_2O$ | $\rightarrow$ | $2\ CN^- + 2\ HCO_3^- +$ $6\ H^+ + 10\ H_2$ | +753 |
| Alanine | | | |
| $2\ H_3C-HCNH_3^+-$ $COO^- + 14\ H_2O$ | $\rightarrow$ | $N_2 + 6\ HCO_3^- +$ $6\ H^+ + 15\ H_2$ | +15 |
| Glutamine | | | |
| $CONH_3^+-H_2C-H_2C-$ $HCNH_3^+-COO^- + 12\ H_2O$ | $\rightarrow$ | $N_2 + 5\ HCO_3^- +$ $6\ H^+ + 12\ H_2$ | |
| Ammonium Hydroxide | | | |
| $2\ NH_4OH$ | $\rightarrow$ | $N_2 + 3\ H_2 + 2\ H_2O$ | +34 |
| Hydroxyl Amine | | | |
| $2\ NH_2OH$ | $\rightarrow$ | $N_2 + H_2 + 2\ H_2O$ | −232 |
| Urea | | | |
| $CO(NH_3)_2^{2+} + 2\ H_2O$ | $\rightarrow$ | $N_2 + HCO_3^- + 3$ $H^+ + 3\ H_2$ | −194 |

An electron acceptor more positive than $N_2/NH_4^+$ would ordinarily be needed to make the oxidation of ammonium chemically spontaneous. However, an applied electrode potential (103), for example set to +500 mV, can be used instead of a chemical electron acceptor to drive the reaction. At +500 mV, the oxidation of ammonium to $N_2$ is spontaneous and hydrogen gas can be produced at the cathode.

Figure 2:
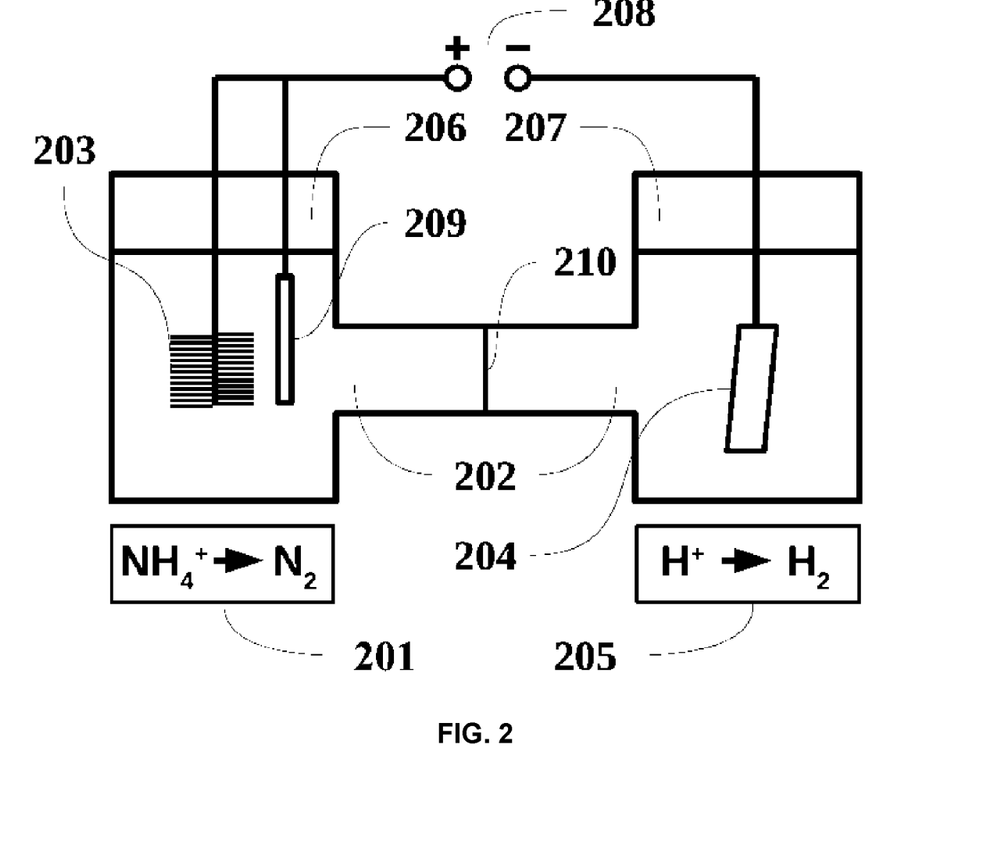
FIG. 2 is a schematic electrolytic cell for carrying out an embodiment, in which ammonium is oxidized while producing hydrogen gas.

FIG. 2 is a schematic of the electrolytic cell used in Example 1 to generate hydrogen gas from an aqueous ammonium solution. In this Example, the cell is divided into a first compartment (206) containing an anode (203) and a second compartment (207) containing a cathode (204). The anode (203) and cathode (204) are partially submerged in an electrolyte (202). The electrolyte (202) also links the two compartments ionically, which were divided by an ion-exchange membrane (210) (Nafion™ 117, Chemours Company, New Castle, Del.). The anode (203) and cathode (204) were in electrical communication with one another via a DC power source (208), the electrolyte (202), and the ion-exchange membrane (210). In Example 1, the DC power source (208) was an AC/DC converter, which is a potentiostat. A reference electrode (209) is provided in order to assist the DC power supply (208) in maintaining a consistent voltage.

Cells of this configuration are described in Siegert et al. "Comparison of Nonprecious Metal Cathode Materials for Methane Production by Electromethanogenesis" *ACS Sustainable Chem. Eng.*, 2014, 2(4), pp 910-917, which is incorporated herein by reference in its entirety.

Each of the reactor chambers (Adams & Chittenden, Berkely, Calif., USA) was sealed using a screw cap (GL45 Corning Screw Caps, Thomas Scientific, Swedesboro, N.J., USA) with a center hole having a septum. The septa were self-made 45 mm discs from 7 mm thick butyl rubber. The two reactor-halves were held together using 35/25 pinch clamps (Thomas Scientific, Swedesboro, N.J., USA).

In other embodiments, the ion-exchange membrane (210) may be omitted. Likewise, the second compartment (207) may further include a collection means for collecting and storing hydrogen gas. Various other DC power sources (208) may also be substituted for the AC/DC converter, such as batteries, solar cells, and the like.

In Example 1, the anode (203) was a cylindrical carbon fiber brush (4 cm×4 cm) made from carbonized polyacrylonitrile fibers sold as Panex 35™ (Zoltek in St. Louis, Mo., USA). Graphite blocks (2×2×0.32 cm) were used as cathode (204), which were sanded with 1,500 grit sandpaper and washed without further treatment. The current collector on the cathode (204) was a titanium wire inserted into the graphite block, through drill holes.

Each electrode was connected to the DC power supply (208) by titanium wires. An Ag/AgCl reference electrode (209) (model RE-5B, BASi, West Lafayette, Ind., USA) was inserted through holes in rubber septa sealing the top of the first (206) compartment.

The solution to be treated in Example 1 was 200 mL of artificial seawater containing 5 mM ammonium chloride and 30 mM sodium bicarbonate. This served as the electrolyte (202), which was added to the first (206) and second (207) compartment. The use of artificial seawater ensured that ammonium was the primary source of electrons and nitrogen in the solution being treated and sodium bicarbonate was the primary carbon source available. A head space of about 50 mL was left in each compartment (206, 207). In alternative embodiments, the electrolye (202) may be municipal wastewater or other nitrogen containing solutions in need of treatment and/or a second electrolyte, such as a suitable buffer, may also be used in the second (207) compartment.

Trace nutrients, minerals, and other growth media were also added to the artificial seawater to support microbial growth. The resulting artificial seawater solution was as follows:

5 mM ammonium chloride
10 mL/L of the following trace element solution:

| | |
|---|---|
| Nitrilotracetic acid | 1.5 g/L |
| $MgSO_4 \times 7H_2O$ | 3 g/L |
| $MnSO_4 \times 2H_2O$ | 0.5 g/L |
| NaCl | 1 g/L |
| $FeSO_4 \times 7H_2O$ | 1 g/L |
| $NiCl_2 \times 6H_2O$ | 0.2 g/L |
| $CoCl_2$ | 0.1 g/L |
| $CaCl_2 \times 2H_2O$ | 0.1 g/L |
| $ZnSO_4$ | 0.1 g/L |
| $CuSO_4 \times 5H_2O$ | 0.01 g/L |
| $AlK(SO_4)_2$ | 0.01 g/L |
| $H_3BO_3$ | 0.01 g/L |
| $Na_2MoO_4 \times 2H_2O$ | 0.01 g/L |
| $Na_2SeO_3 \times 5\ H_2O$ | 0.01 g/L |
| $Na_2WO_4 \times 2\ H_2O$ | 0.01 g/L |

10 mL/L of the following vitamin solution:

| | |
|---|---|
| Pyridoxin × 2HCl | 50 mg/L |
| Thiamin × 2HCl | 10 mg/L |
| $B_{12}$ (cyanocobalamine) | 10 mg/L |
| p-Aminobenzoic acid | 10 mg/L |
| Riboflavin | 5 mg/L |
| Nicotinic acid | 5 mg/L |
| Ca—D(+)-pantothenate | 5 mg/L |

-continued

| Lipoic (thioctic) acid | 5 mg/L |
| D(+)-biotin | 2 mg/L |
| Folic acid | 2 mg/L |

Each litre of artificial seawater further contained:

| $KH_2PO_4$ | 0.20 g |
| $NaHCO_3$ | 0.25 g (30 mM) |
| $NH_4Cl$ | 0.25 g |
| KCl | 0.72 g |
| KBr | 0.09 g |
| $CaCl_2 \times 2H_2O$ | 1.40 g |
| $MgCl_2 \times 6H_2O$ | 5.7 g |
| $MgSO_4 \times 7H_2O$ | 6.8 g |
| NaCl | 26 g |

Further details are provided in Siegert M, Sitte J, Galushko A, Kruger M (2014a), "Starting up microbial enhanced oil recovery." In: Schippers A, Glombitza F, Sand W (eds) *Geobiotechnology II*. Springer Berlin Heidelberg, pp 1-94, which is incorporated herein by reference in its entirety.

The first compartment (206) of the electrolytic cell was also inoculated with ocean floor sediment from one of three different locations in the Atlantic Ocean, off the coast of Namibia. Three separate inocula (301, 302, 303) were collected from ocean sediments using gravity corers. The first inoculum (301) was collected at 25°45.060S and 13°04.200E at a water depth of 1,942 m and a sediment depth of 308 cm. The second inoculum (302) was collected at 26°22.178S and 11°53.492E in 3795.6 m water and 0-431 cm sediment depth. The third inoculum (303) was collected at 27°44.131S and 14°14.553E in 1249.3 water and 8-88 cm sediment depth. Live cultures were taken using 1 mL of gravity core sediment, diluted 1/5 with on-site seawater and stored over several years. One mL of the 1/5 (i.e. 20%) dilution was used to inoculate the first compartment (206). Without committing to a particular theory, it is believed that this mixed ocean floor inoculum contained a variety of microorganisms from various genera, including electrogenic species.

In operation, the power supply (208) was adjusted to maintain +400 mV or +550 mV at the anode (203), depending on the treatment. Potentials reported here are expressed versus a standard hydrogen electrode (SHE), which has an approximate offset potential to an Ag/AgCl electrode of about +0.2 volts.

The cells were operated in fed-batch cycles in which the anode (203) was poised at +550 mV during the first two cycles (304, 305) and at +400 mV during the last three cycles (306, 307, 308) using a potentiostat as the power source (208). All voltages are versus a standard hydrogen electrode.

While both compartments were batch-fed, only the first compartment (206) was inoculated with microorganisms. Re-inoculation of the first compartment (206) was carried out with a 10% volume of the solution from the previous batch cycle, resulting a 10-fold dilution series of the existing microorganisms in the first compartment (206). That is, at the end of one fed-batch cycle, 90 mL of solution from the first compartment (206) was discarded. The remaining 10 mL were mixed with 90 mL fresh solution to create a 1:9 mix, which was used to fill the first compartment (206) and the fed batch cycle was started anew. In contrast, the second compartment (207) was completely replenished with fresh electrolyte (202) on each feeding.

Prior to the start of each fed-batch cycle, the headspace in each compartment (206, 207) was flushed using argon gas for at least 5 minutes. This created a substantially anaerobic environment in the electrolytic cell and allowed for more accurate measurements of nitrogen gas production. The anodic potentials used (i.e. +400 mV to +500 mV) were also too low to cause formation of secondary $O_2$ within the cell through electrolysis of water, which can occur at higher potentials (i.e. +820 mV with Pt catalyst).

Each batch cycle was operated at room temperature (i.e. between 20-30° C.) and standard atmospheric pressure. The total length of the experiment was 600 days.

Figure 3A:
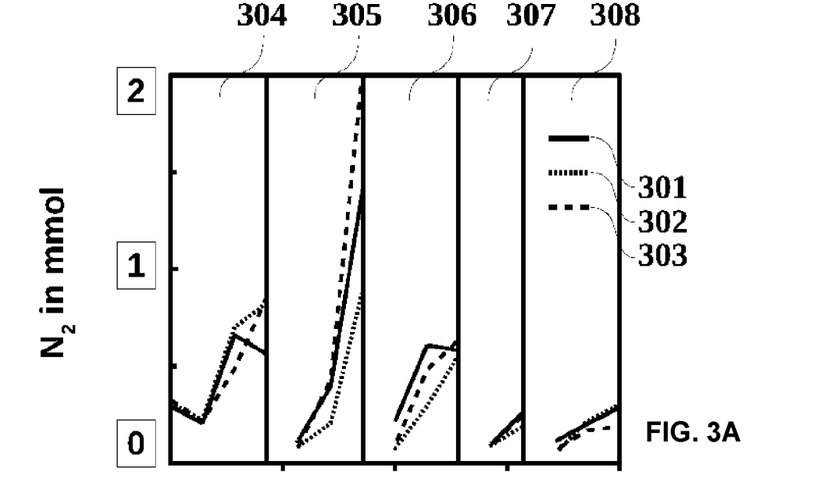
FIG. 3A depicts nitrogen evolution in an electrolytic embodiment over two fed-batch cycles (304, 305) poised at +0.550 volts and three subsequent cycles (306, 307, 308) poised at +0.4 volts. All voltages are versus a standard hydrogen electrode. The results using microbial innocula derived from three separate locations on the ocean floor (301, 302, 303) are shown.

FIG. 3A depicts nitrogen evolution in the electrolytic cell over five fed-batch cycles (304, 305, 306, 307, 308) with ammonium as the only source of electrons and nitrogen. The results for three electrolytic cells are shown. Each cell was inoculated with one of the three ocean floor sediments (301, 302, 303).

Figure 3B:
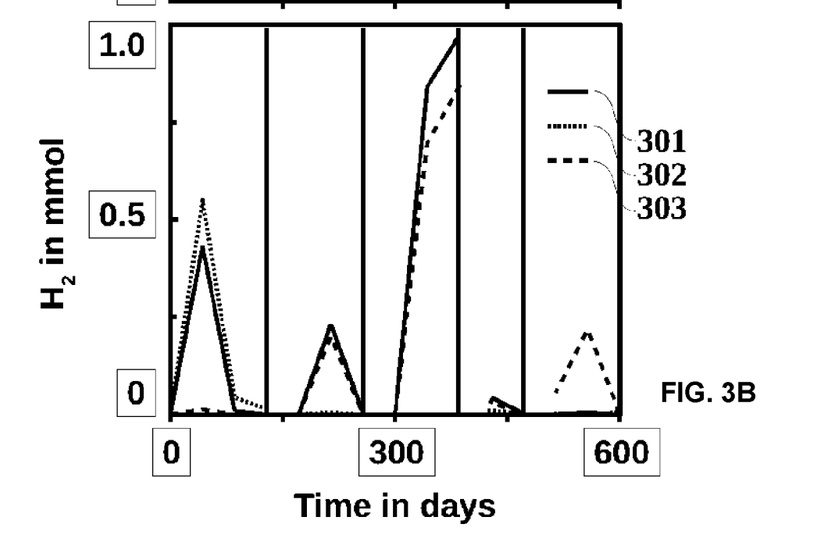
FIG. 3B depicts hydrogen evolution in an electrolytic embodiment over two fed-batch cycles (304, 305) poised at +0.55 volts and the three subsequent cycles (306, 307, 308) poised at +0.4 volts. All voltages are versus a standard hydrogen electrode. The results using microbial innocula derived from three separate locations on the ocean floor (301, 302, 303) are shown.

FIG. 3B depicts hydrogen evolution in the electrolytic cell over five fed-batch cycles (304, 305, 306, 307, 308) with ammonium as the only source of electrons and nitrogen. The results for three electrolytic cells are shown. Each cell (301, 302, 303) was inoculated with one of the three ocean floor sediments (301, 302, 303).

The above experiment was repeated by the inventor, with similar results.

The predicted half reactions are as follows:

Without necessarily committing to a particular theory, it is believed that the microorganisms formed a biofilm on the anode (203). In a first reaction zone, these microorganisms transferred electrons from the oxidation reaction (201) into the anode (203), which passed to the cathode (204) via the power supply (208) under the applied voltage. Simultaneously, hydrogen ions generated during the oxidation reaction (101) in the first reaction zone migrated across the membrane (210), and into the second compartment (207). In the second compartment (207), electrons arriving from the cathode (204) and hydrogen ions arriving from the first compartment (206) are consumed in a reduction reaction (205) at a second reaction zone around the cathode (204).

Example 2

Electrolytic Denitrification Coupled to Methane Gas Production

Figure 4:
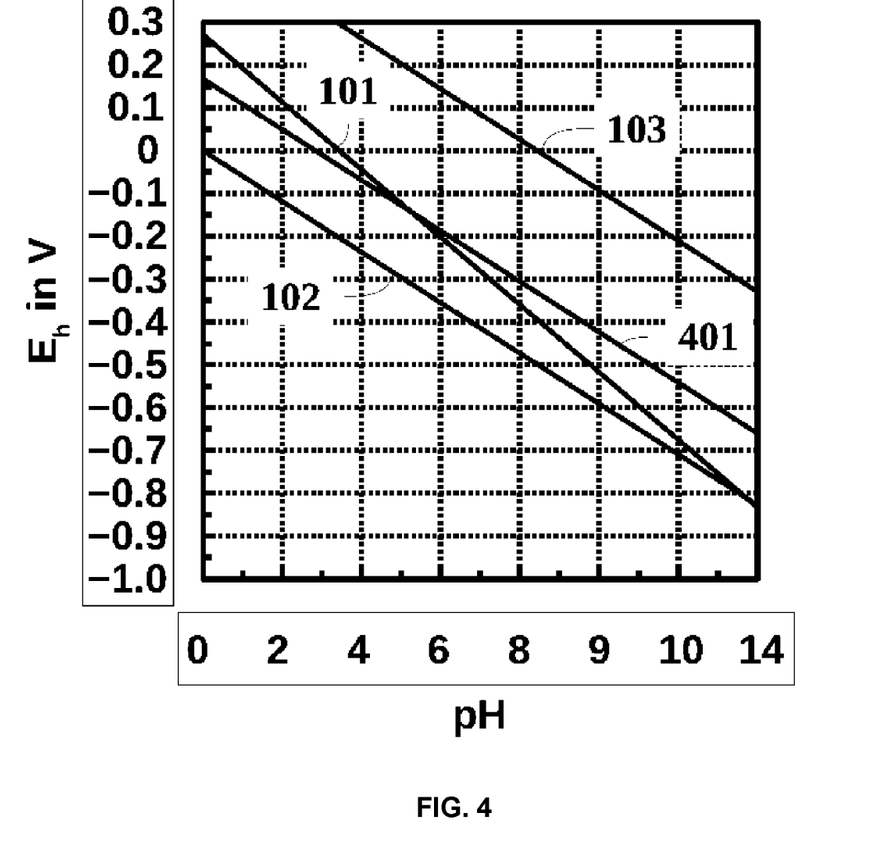
FIG. 4 is a Pourbaix diagram showing the relationship between pH and redox potentials $E_h$ of ammonium oxidation (101), proton reduction (102), $CO_2$ reduction to methane (401), and proton reduction at +0.5 volts (103). All voltages are versus a standard hydrogen electrode.

FIG. 4 is a Pourbaix diagram showing the relationship between pH and redox potentials $E_h$ of ammonium oxidation (101), proton reduction (102), and $CO_2$ reduction to methane (401). Also shown is the hypothetical offset potential of proton reduction (103) at +0.5 volts, for comparison.

TABLE 2

Gibbs Free Energy for complete reactions for the oxidation of various nitrogen-containing compounds using carbon dioxide as the oxidant:

| Net reaction | $\Delta G^{o\prime}$ kJ mol$^{-1}$ |
|---|---|
| Ammonium | |
| $8\ NH_4^+ + 3\ HCO_3^- \rightarrow 4\ N_2 + 3\ CH_4 + 5\ H^+ + 9\ H_2O$ | −90 |
| $3\ NH_4^+ + HCO_3^- \rightarrow N_3^- + CH_4 + 3\ H^+ + 3\ H_2O$ | +271 |
| $2\ NH_4^+ + HCO_3^- \rightarrow N_2O + CH_4 + H^+ + 2\ H_2O$ | +284 |
| $8\ NH_4^+ + 5\ HCO_3^- \rightarrow 8\ NO + 5\ CH + 3\ H^+ + 7\ H_2O$ | +2,237 |
| $4\ NH_4^+ + 3\ HCO_3^- \rightarrow 4\ NO_2^- + 3\ CH_4 + 5\ H^+ + H_2O$ | +1,341 |
| $4\ NH_4^+ + 3\ HCO_3^- \rightarrow 2\ N_2O_3 + 3\ CH_4 + H^+ + 3\ H_2O$ | +1,459 |
| $8\ NH_4^+ + 7\ HCO_3^- \rightarrow 4\ N_2O_4 + 7\ CH_4 + H^+ + 5\ H_2O$ | +3,561 |
| $8\ NH_4^+ + 7\ HCO_3^- \rightarrow 8\ NO_2 + 7\ CH_4 + H^+ + 5\ H_2O$ | +3,572 |
| $NH_4^+ + HCO_3^- \rightarrow NO_3^- + CH_4 + H^+$ | +464 |
| $2\ NH_4^+ + 2\ HCO_3^- \rightarrow N_2O_5 + 2\ CH_4 + H_2O$ | +1,111 |
| Ethyl Amine | |
| $8\ H_3C-CH_2NH_3^+ + 3\ H_2O \rightarrow 4\ N_2 + 15\ CH_4 + HCO_3^- + 9\ H^+$ | −1,285 |
| $4\ H_3C-CH_2NH_3^+ + HCO_3^- \rightarrow 4\ CN^- + 5\ CH + 7\ H^+ + 3H_2O$ | +828 |
| Alanine | |
| $8\ H_3C-HCNH_3^+-COO^- + 11\ H_2O \rightarrow 4\ N_2 + 15\ CH_4 + 9\ HCO_3^- + 9\ H^+$ | −1,974 |
| Glutamine | |
| $CONH_3^+-H_2C-H_2C-HCN\ H_3^+-COO^- + 3\ H_2O \rightarrow N_2 + 3\ CH + 2\ HCO_3^- + 3\ H^+$ | −507 |
| Ammonium Hydroxide | |
| $8\ NH_4OH + 3\ HCO_3^- + 3\ H^+ \rightarrow 4\ N_2 + 3\ CH_4 + 17\ H_2O$ | −272 |
| Hydroxyl Amine | |
| $8\ NH_2OH + HCO_3^- + H^+ \rightarrow 4\ N_2 + CH_4 + 11\ H_2O$ | −1,063 |
| Urea | |
| $4\ CO(NH_3)_2^{2+} \rightarrow 4\ N_2 + 3\ CH_4 + HCO_3^- + 9\ H^+ + H_2O$ | −1,181 |

As seen in FIG. 4 and Table 2, the oxidation of ammonium using carbon dioxide as the oxidant proceeds spontaneously ($\Delta G^{o\prime} = -90$ kJ mol$^{-1}$), as follows:

$8NH_4^+ + 3HCO_3^- \rightarrow 3CH_4 + 4N_2 + 5H^+ + 9H_2O$

Accordingly, one advantage of producing methane gas is that a power supply is not always required to drive the reaction. Nevertheless, the application of a potential can increase the kinetics of the reaction.

Figure 5:
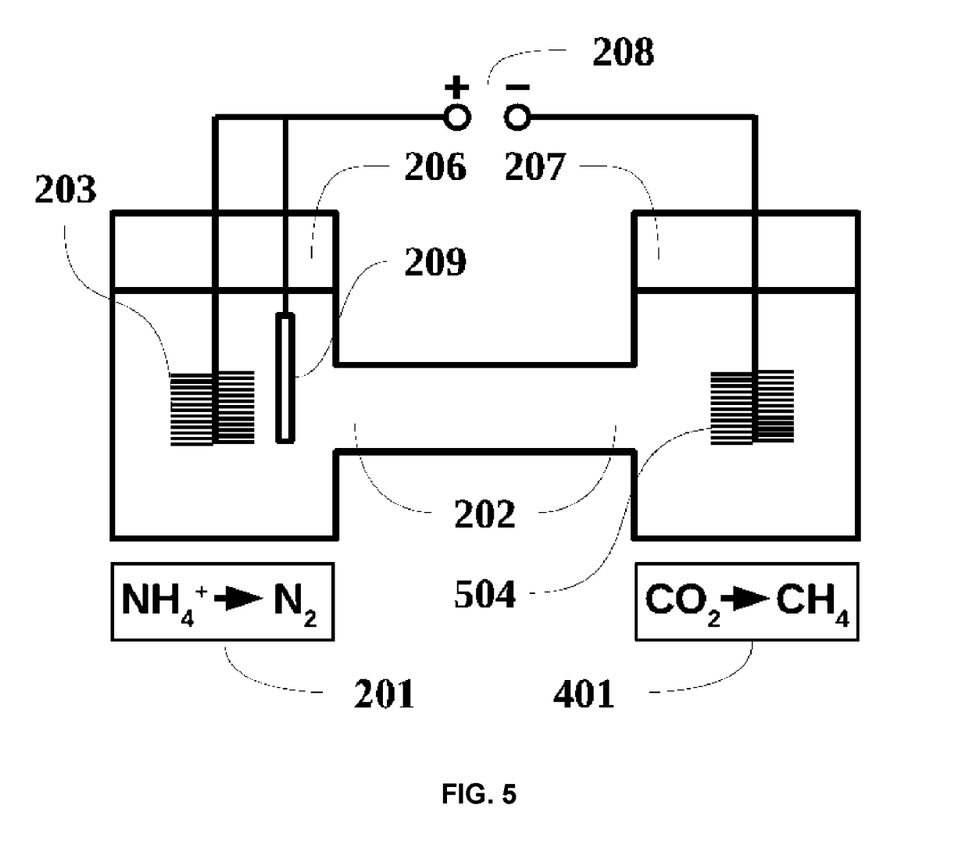
FIG. 5 is a schematic electrolysis reactor carrying out an embodiment, in which ammonium is oxidized while producing methane gas.

FIG. 5 is a schematic of the electrolytic cell used in Example 2, which is substantially the same construction as in Example 1. However, in this example, the ion-exchange membrane (210) was omitted so as to allow free movement of microorganisms between the first (206) and second (207) compartments.

In other embodiments, the ion-exchange membrane (210) may be included, as shown in FIG. 2. Likewise, the second compartment (207) may further include a collection means for collecting and storing methane.

Two configurations were tested for the anode (203), with three replicate electrolytic cells in each configuration. In the first configuration, cylindrical carbon fiber brushes (4 cm×4 cm) made from carbonized polyacrylonitrile fibers sold as Panex 35™ (Zoltek in St. Louis, Mo., USA) were used as the anode (203). In the second configuration, a "drum" style anode (601) was used, which comprised a cylindrical titanium mesh basket (4 cm×4 cm, mesh size 40, Ti wire as current collector) with a closed top and bottom, in which the basket was filled with untreated graphite granules of 0.5-5 mm diameter and irregular shapes. Electrodes of this type are described by Siegert in PCT application No. PCT/IB2018/052671, filed April 2018, which is incorporated by reference herein. The cathodes (504) were untreated 4 cm×4 cm stainless steel brushes (type 304) purchased from Gordon Brush in Commerce, Calif., USA.

In operation, the power supply (208) was adjusted to maintain +500 mV at the anode (203). Potentials reported here are expressed versus a standard hydrogen electrode (SHE), which has an approximate offset potential to an Ag/AgCl electrode of about +0.2 volts.

The solution to be treated was domestic wastewater collected at Calgary's Fish Creek Wastewater Treatment Plant, usually during the morning hours. Pure wastewater was obtained from the primary clarifier. Total Kjeldah Nitrogen ("TKN") concentrations varied from 43 to 120 mg/L (N) or 3-9 mM.

In Example 2, the microorganisms were provided endogenously within the wastewater, which was enriched by a 1% inoculum of anaerobic digester sludge obtained from the same wastewater treatment plant. This wastewater solution was supplied to the first (206) and second (207) compartments of the electrolytic cell. In alternative embodiments, a different electrolyte, such as a suitable buffer, may instead be used in the second (207) compartment, in place of wastewater.

Without committing to a particular theory, it is believed that the inoculum derived from the wastewater and anaerobic digester sludge contained a variety of microorganisms from various genera, including electrogenic and methanogenic species.

Once the experiment was underway, no additional inoculum was used from the anaerobic digester. Instead, the electrolytic cells were batch fed using a 10% volume of solution from the previous batch cycle mixed with freshly collected wastewater, resulting a 10-fold dilution series. Each fed-batch cycle lasted until gas evolution ceased but no longer than ten days. Each batch cycle was operated at room temperature (i.e. between 20-30° C.) and standard atmospheric pressure.

Each cell was operated as a closed system, such that oxidative decomposition of organic and other materials in the wastewater quickly created an anaerobic environment within the cells. The anodic potentials used (i.e. 0.5 volts) were also too low to cause formation of secondary $O_2$ within the cell through electrolysis of water, which can occur at higher potentials (i.e. +0.82 volts with a Pt catalyst). The average $O_2$ concentration within the wastewater was 42±34 µM with the error being the standard deviation, n=392 measurements. On average, there was a slight increase in $O_2$ levels within the head space (1 µM/day) due to sampling and leakage. Nevertheless, $O_2$ concentrations within the wastewater continued to decrease over the course of the experiment. The maximum observed $O_2$ concentration within the wastewater was approximately 80 µM at one measurement. $O_2$ concentrations of less than 100 µM, less than 50 µM, and less than 30 µM are also contemplated within the scope of the present disclosure.

In Example 2, the oxidant was carbon dioxide, which was reduced to methane. The $CO_2$ in the cathode reaction (205) may be in the form of bicarbonate ions within the wastewater to be treated (e.g. due to the previous oxidation of organic molecules in the wastewater) or can be supplied to the electrolytic cell by an outside source, such as $CO_2$ sparging or gaseous supply to the head space in the second compartment (207).

Figure 6A:
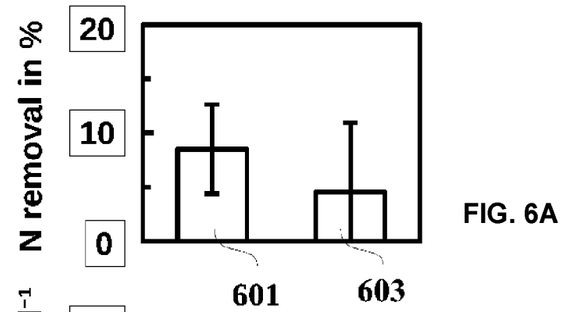
FIG. 6A depicts the % Nitrogen removal in an embodiment using a carbon brush anode (601) or a graphite granule "drum" anode (603).

FIG. 6A depicts the % nitrogen removal using a carbon brush anode (603) or a graphite granule "drum" anode (601). Total nitrogen was determined using the TKN method.

Figure 6B:
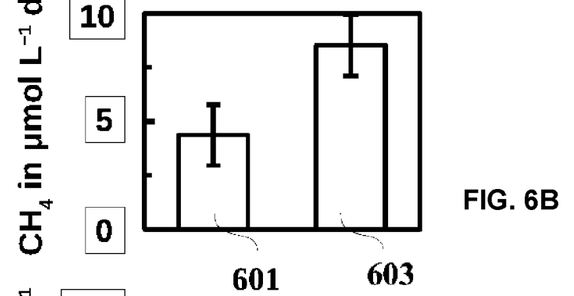
FIG. 6B depicts the combined evolution of methane on the cathode and the anode in μmol/L/day using a carbon brush anode (601) or a graphite granule "drum" anode (603) in an embodiment.

FIG. 6B depicts the combined evolution of methane from both compartments (206, 207) in μmol/L/day using a carbon brush anode (603) or a graphite granule "drum" anode (601) of the type described above. The cathodes were in all cases the steel brushes described above. Gases were measured using a gas chromatograph. During the first four fed-batch cycles, the second compartment (207) also produced hydrogen gas (not shown) which was consumed by methanogenic microorganisms and converted into methane gas. During the last fed-batch cycle, hydrogen gas accumulated only during the first day.

Figure 6C:
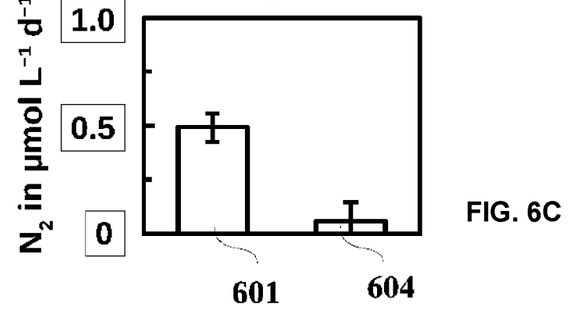
FIG. 6C depicts the evolution of nitrogen gas in μmol/L/day at the anode (203) or a cathode (604) of an embodiment.

FIG. 6C depicts the evolution of nitrogen gas in μmol/L/day at the anode (601) and cathode (604) of the electrolytic cells. A graphite granule "drum" style anode (601) was used in this experiment, which was performed in triplicate. As seen in FIG. 6C, there was more dinitrogen gas in the anode compartment than in the cathode compartment indicating an oxidative process, which in the case of wastewater can be the oxidation of organic nitrogen or ammonium.

The predicted half reactions are as follows:

Without necessarily committing to a particular theory, it is believed that microorganisms populated both the anode (203) and the cathode (504) of the electrolytic cell. Electrons and hydrogen ions were transferred from the oxidation reaction (201) in a first reaction zone around the anode (203) to a second reaction zone around the cathode (504), in a similar manner to Example 1 above. In Example 2, microorganisms were also present in the second compartment (207), possibly as a biofilm on the cathode (504). It is believed that methanogens amongst the population of micoorganisms were responsible for the reduction reaction (401), in which incoming hydrogen ions from the electrolyte (202) were combined with incoming electrons from the cathode (504) in the presence of bicarbonate, at a second reaction zone in the second compartment (207), to produce methane and water. Intermediates in this process may include hydrogen gas, which is likely consumed by the methanogens when producing methane.

Example 3

Fuel Cell Nitrogen Removal

Figure 7:
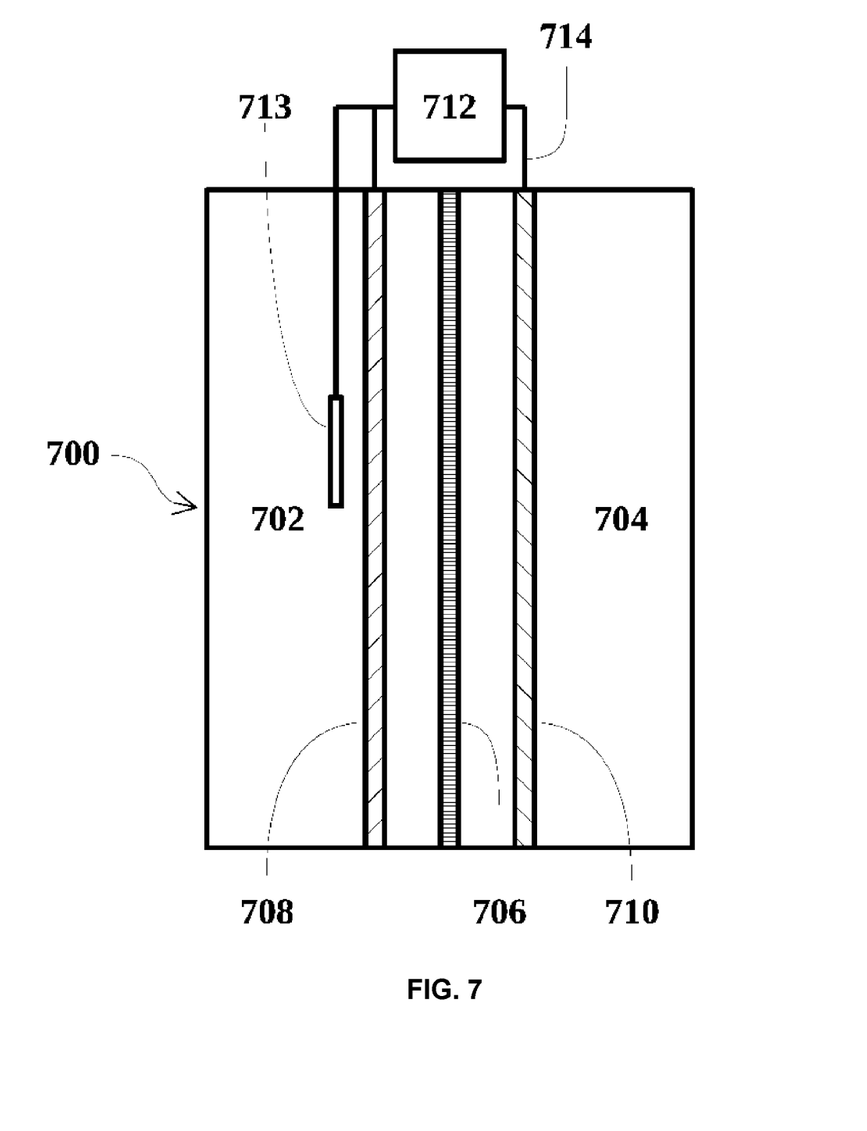
FIG. 7 depicts a fuel cell which includes an anode compartment and a cathode compartment.

Referring to FIG. 7, in another aspect, there is provided a fuel cell (700). The fuel cell (700) includes an anode compartment (702) and a cathode compartment (704). The anode compartment (702) is separated from the cathode compartment (704) by a separator (706) configured to permit selective permeation of ionic species therethrough. An anode (708) is disposed within the anode compartment (702) and a cathode (710) is disposed within the cathode compartment (704). The anode (708) and cathode (710) are electrically coupled to an external load (712) via an external circuit (714). A reference electrode (713) may be used to monitor the redox potential at either of the electrodes.

Although control over the voltage may be more difficult, a fuel cell (700) is more efficient as it avoids two energy conversion steps typical of electrolytic arrangements, namely: (a) conversion of electricity into chemical energy; and (b) conversion of chemical energy back into electricity.

Wastewater is supplied to the anode compartment (702) such that the wastewater becomes disposed within the anode compartment (702) in electrical communication with the anode (708). In some embodiments, for example, the wastewater includes nitrogen-containing or organic compounds that serve as the energy source for the fuel cell.

Oxidant is supplied to the cathode compartment (704) such that the oxidant becomes disposed within the cathode compartment (704) in electrical communication with the cathode (710). Such an oxidant may be gaseous oxygen dissolved in solution but can be any other oxidizing compound. In some embodiments, for example, the oxidant includes $O_2$, benzoyl peroxide, ferricyanide, manganese dioxide, or nitrate.

Mediated by electrical communication, the oxidant reacts with a fuel source to create a cathodic reduction reaction with a redox potential more positive than the anodic oxidation reaction. Example compounds that may serve as the energy source for the fuel cell include nitrogen-containing compounds and organic compounds, which may be found in wastewater or may be supplied separately to the cathode compartment (704). Examples fuel sources include ammonium, benzylamine, ethanolamine, arginine, cysteine, serine, acetamide, N-methylacetamide, or other nitrogen-containing compounds.

An example of such a reaction mediated by the fuel cell (700) is the oxidation of ammonium in the presence of molecular oxygen (2 $NH_4^+$+3 $O_2 \rightarrow$2 $N_2$+4 $H^+$+6 $H_2O$; $\Delta G°$=−1,265 kJ mol$^{-1}$). Various other nitrogen-containing compounds or organic molecules may be similarly oxidized to provide the required current.

While: (i) the wastewater is disposed in electrical communication with the anode (708), and (ii) the oxidant is disposed in electrical communication with the cathode (710), electrical current is generated across the external circuit (714) of the fuel cell (700). Such current may be used to drive the anodic reaction and/or be used to power a useful external load (712) such as a resistor or battery.

In some embodiments, a plurality of microorganisms may be disposed within the anode compartment (702) to assist the anodic reaction. In some embodiments, for example, at least a portion of such microorganisms may be coated on the anode (708) as a biofilm. These microorganisms may assist in nitrogen removal in the manner described in Examples 1 and 2 above.

In yet another aspect, the electrochemical cell in Example 2 (see: FIG. 5) may itself be configured as a microbial fuel cell. As discussed, the oxidation of ammonium using carbon dioxide under anaerobic conditions is a spontaneous reaction ($\Delta G°'$=−90 kJ mol$^{-1}$). In this embodiment, the power supply (208) is replaced by a useful electrical circuit, and the voltage potential is generated by spontaneous oxidation of nitrogen-containing compounds by electrogenic microorganisms at the anode (203).

In yet another aspect, the fuel cell (700) can be used for detecting target material within the wastewater, and the load (712) is an electrical current sensor. In this respect, in some embodiments, for example, the disposition of the wastewater within the fuel cell (700) is with effect that an electrical current is generated that is representative of the presence of a target material within the wastewater. The sensing of the current by the sensor can be used to indicate detection of the target material within the wastewater. In response to the sensing, a signal can be transmitted, representative of the detection of the target material. Examples of such targets include nitrogen-containing compounds.

The detection of nitrogen-containing compounds may be used as a signal to begin treating the wastewater, suspending the treatment of the wastewater, increasing a stimulus applied to the wastewater for the treatment of wastewater, or decreasing a stimulus applied to the wastewater for the treatment of wastewater. The stimulus may include admixing the wastewater with a reagent, or disposing the wastewater within a reaction zone in the electrolytic cell, with effect that the aqueous solution is in electrical communication with an anode and the anode is disposed in electrical communication with a cathode and applying a voltage, and includes embodiments discussed herein.

The embodiments of the present disclosure are intended to be examples only. Those of skill in the art may effect alterations, modifications and variations to the particular embodiments without departing from the intended scope of the present application.

In particular, features from one or more of the above-described embodiments may be selected to create alternate embodiments comprised of a subcombination of features which may not be explicitly described above. In addition, features from one or more of the above-described embodiments may be selected and combined to create alternate embodiments comprised of a combination of features which may not be explicitly described above. Features suitable for such combinations and subcombinations would be readily apparent to persons skilled in the art upon review of the present application as a whole. The subject matter described herein and in the recited claims intends to cover and embrace all suitable changes in technology.

The invention claimed is:

1. A method of treating an aqueous solution and producing methane using an electrolytic cell comprising an anode, a cathode, an aqueous electrolyte effecting ionic communication between the anode and the cathode, and operative microorganisms disposed relative to the anode and the cathode in the cell or on the anode wherein the anode is electrically coupled to the cathode, the method comprising:
   establishing a reactive process, including:
      supplying the aqueous solution to the electrolytic cell such that the aqueous solution becomes disposed in electrical communication with the anode, the aqueous solution comprising at least one nitrogen-containing compound;
   supplying an oxidant to the electrolytic cell such that the oxidant becomes disposed in electrical communication with the cathode;
   wherein the supplying of the aqueous solution and the supplying of an oxidant cooperate with effect that:
   (i) electrolytic oxidation of the at least one nitrogen-containing compound is facilitated at the anode by the operative microorganisms; and
   (ii) the oxidant is reduced at the cathode to produce methane; and
   collecting the produced methane;
   wherein the oxidant comprises carbon dioxide, and the electrolytic cell contains less than 100 µmol $L^{-1}$ of free oxygen.

2. The method of claim 1, wherein the free oxygen is $O_2$.

3. The method of claim 2, wherein the oxidation of the at least one nitrogen-containing compound is with effect that gaseous nitrogen is produced in a zone containing the anode.

4. The method of claim 1, wherein the microorganisms form a biofilm on the anode.

* * * * *